United States Patent
Chen et al.

(10) Patent No.: US 10,214,506 B2
(45) Date of Patent: Feb. 26, 2019

(54) PREPARATION METHOD FOR 2-((4R,6S)-6-BROMOMETHYL-2-OXO-1,3-DIOXANE-4-YL)ACETATE

(71) Applicant: FUDAN UNIVERSITY, Shanghai (CN)

(72) Inventors: Fener Chen, Shanghai (CN); Guanxin Huang, Shanghai (CN); Ge Meng, Shanghai (CN); Minjie Liu, Shanghai (CN); Yan Wu, Shanghai (CN); Dang Cheng, Shanghai (CN); Zedu Huang, Shanghai (CN); Haihui Peng, Shanghai (CN); Fangjun Xiong, Shanghai (CN)

(73) Assignee: FUDAN UNIVERSITY, Shanghai (CN)

(*) Notice: Subject to any disclaimer, the term of this patent is extended or adjusted under 35 U.S.C. 154(b) by 0 days.

(21) Appl. No.: 15/871,049

(22) Filed: Jan. 14, 2018

(65) Prior Publication Data
US 2018/0339974 A1 Nov. 29, 2018

(30) Foreign Application Priority Data
May 25, 2017 (CN) .......................... 2017 1 0380639

(51) Int. Cl.
*C07D 319/06* (2006.01)
*C07B 47/00* (2006.01)
*C07B 41/12* (2006.01)

(52) U.S. Cl.
CPC ............ *C07D 319/06* (2013.01); *C07B 41/12* (2013.01); *C07B 47/00* (2013.01)

(58) Field of Classification Search
None
See application file for complete search history.

*Primary Examiner* — Heidi Reese
(74) *Attorney, Agent, or Firm* — Wayne & Ken, LLC; Tony Hom

(57) ABSTRACT

The present disclosure belongs to the technical field of organic synthesis and particularly relates to a preparation method for 2-((4R,6S)-6-bromomethyl-2-oxo-1,3-dioxane-4-yl)acetate. The 2-((4R,6S)-6-bromomethyl-2-oxo-1,3-dioxane-4-yl)acetate is a key chiral intermediate for preparation of statin antilipemic agents. In the present disclosure, the 2-((4R,6S)-6-bromomethyl-2-oxo-1,3-dioxane-4-yl)acetate is obtained by bromination and cyclization of 3-((substituted oxycarbonyl)oxy)-5-hexenoate as raw material with hypochlorite and bromide in an organic solvent in the presence of $CO_2$. The method of the present disclosure has the advantages of readily available raw material, mild reaction conditions, easy operation, low cost, excellent atomic economy and less by-products, and is applicable to industrial production.

6 Claims, No Drawings

PREPARATION METHOD FOR 2-((4R,6S)-6-BROMOMETHYL-2-OXO-1,3-DIOXANE-4-YL)ACETATE

TECHNICAL FIELD

The present disclosure belongs to the technical field of organic synthesis and particularly relates to a preparation method for 2-((4R,6S)-6-bromomethyl-2-oxo-1,3-dioxane-4-yl)acetate.

BACKGROUND

As an organic synthetic intermediate, 2-((4R,6S)-bromomethyl-2-oxo-1,3-dioxane-4-yl)acetate can be used for synthesis of statin antilipemic agents. Its chemical formula is shown in (I):

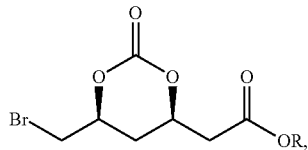

wherein R is alkyl or cycloalkyl having 1 to 8 carbon atoms, or mono- or poly-substituted aryl or aralkyl.

Chinese Patent CN104356109 disclosed a method for preparing 2-((4R,6S)-6-bromomethyl-2-oxo-1,3-dioxane-4-yl)acetate (I) by bromination and cyclization of 3-((substituted oxycarbonyl)oxy)-5-hexenoate as raw material with brominating agent and alkali.

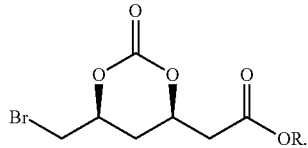

By this method, about 20% of the by-products resulted from the addition reaction of alkene and dibromo will be generated in addition to about 80% of the target product (I).

In Chinese Patent CN106588865, 2-((4R,6S)-6-bromomethyl-2-oxo-1,3-dioxane-4-yl)acetate (I) is prepared by bromination and cyclization of 3-((substituted oxycarbonyl)oxy)-5-hexenoate as also the same raw material with bromide and oxidant.

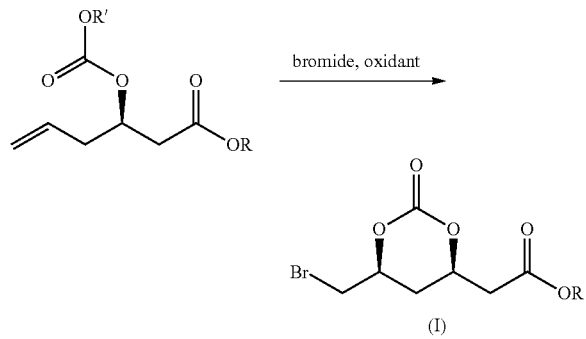

This method avoids the generation of dibromo by-products and thus has the certain technical advantages. However, this method has the detects of using the protective group, i.e., substituted oxycarbonyl, which resulted in the complicated starting material with a high molecular weight for the synthesis and is removed as waste after the reaction. Therefore, this method is high in cost and low in atomic economy.

Accordingly, it is necessary to develop an industrial production process for preparing 2-((4R,6S)-6-bromomethyl-2-oxo-1,3-dioxane-4-yl)acetate (I) with high efficiency, low cost and excellent atomic economy.

SUMMARY

An objective of the present disclosure is to provide a novel method for preparing 2-((4,6S)-6-bromomethyl-2-oxo-1,3-dioxane-4-yl)acetate (I) with simple process, low cost and reduced pollution, in order to make up the shortage of the prior art.

In the preparation method for 2-((4R,6S)-6-bromomethyl-2-oxo-1,3-dioxane-4-yl)acetate (I) provided by the present disclosure, 2-((4R,6S)-6-bromomethyl-2-oxo-1,3-dioxane-4-yl)acetate (I) is obtained by bromination and cyclization of 3-((substituted oxycarbonyl)oxy)-5-hexenoate (II) as raw material with hypochlorite and bromide in an organic solvent in the presence of $CO_2$. The synthetic route is as follows:

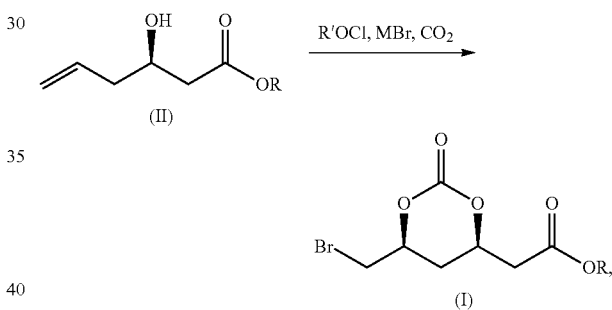

wherein R and R' are the same or different alkyl or cycloalkyl having 1 to 8 carbon atoms, or mono- or poly-substituted aryl or aralkyl; and M is alkali metal, alkaline earth metal or ammonium cation.

Compared with the traditional processes, the method of the present disclosure omits the protection step by substituted oxycarbonyl. The involved oxidant i.e., hypochlorite, has the advantages of low molecular weight, easy preparation and low cost. This method can greatly reduce the production cost and reduce pollution. It has the excellent atomic economy and is applicable to industrial production for large scale process.

The starting material in the present disclosure, i.e., the compound (R)-3-hydroxy-5-hexenoate (II), can be prepared with reference to the International Patent WO2003053950 or Chinese Patent CN101735272. The hypochlorite used in preparation of the compound (I) from the compound (II) is ethyl hypochlorite, isopropyl hypochlorite, tert-butyl hypochlorite or the like. The hypochlorite can be prepared with reference to U.S. Pat. No. 2,694,722. The used inorganic bromide is selected from potassium bromide, sodium bromide, ammonium bromide and the like. The used organic solvent is selected from ethyl acetate, dichloromethane, tedrahydrofuran, methanol, acetic acid, N,N-dimethyl formamide, acetone and acetonitrile, or is a mixed solvent of more of the above solvents. Those solvents are inexpensive and readily available, and have been widely used in the pharmaceutical and chemical industries.

In the present disclosure, a mole ratio of the compound (II) to hypochlorite to inorganic bromide is 1:(1-5):(1-5), and the reaction temperature is −60° C. to 50° C. $CO_2$ may be under a normal pressure or an increased pressure. The reaction may be operated conveniently under a pressure of 0.1 MPa to 2 MPa. The reaction time ranges from 10 mins to 180 mins.

In the present disclosure, preferably:

during preparation of the compound (I) from the compound (II), the used hypochlorite is tert-butyl hypochlorite, the used bromide is potassium bromide, and the used organic solvent is dichloromethane.

A mole ratio of the compound (II) to hypochlorite to bromide is 1:(1.5-2.5):(1.5-2.5), the reaction temperature is −40° C. to 25° C., $CO_2$ is under a pressure of 0.1 MPa to 1 MPa, and the reaction time is 30 mins to 60 mins.

The present disclosure has the advantages of the readily available and inexpensive raw material, mild reaction conditions, easy operation, simple process, efficient synthesis method and environmental protection, which is quite applicable to industrial production of this important intermediate.

DETAILED DESCRIPTION OF THE DISCLOSURE

The present disclosure will be further described by embodiments. But the present disclosure is not limited thereto.

Embodiment 1

(R)-3-hydroxy-5-tert-butyl hexenoate (1.86 g), potassium bromide (2.38 g) and dichloromethane (20 mL) were placed in an autoclave; $CO_2$ (0.5 MPa) was filled; tert-butyl hypochlorite (1.63 g) as added dropwise while stirring the mixture at −20° C.; at the end of dropwise addition of tert-butyl hypochlorite, the mixture was stirred for 60 mins while being kept at a certain temperature; at the end of reaction, 10% sodium sulfite solution (15 mL) was added in the mixture; the reaction liquid was extracted with dichloromethane; and the organic phase was collected, washed with saturated sodium bicarbonate solution, dried with anhydrous sodium sulfate, and concentrated to obtain a light yellow solid crude product. The crude product was washed with petroleum ether (25 mL) to obtain a white powdery solid 2-((4R,6S)-6-bromomethyl-2-oxo-1,3-dioxane-4-yl) tert-butyl acetate (2.62 g, 85%).

Embodiment 2

(R)-3-hydroxy-5-methyl hexenoate (1.44 g), potassium bromide (2.38 g) and acetonitrile (20 mL) were placed in an autoclave; $CO_2$ (2 MPa) was filled; tert-butyl hypochlorite (2.17 g) was added dropwise while stirring the mixture at 0° C.; at the end of dropwise addition of tert-butyl hypochlorite, the mixture was stirred for 30 mins while being kept at a certain temperature; at the end of reaction, 10% sodium sulfite solution (15 mL) was added in the mixture; the reaction liquid was extracted with ethyl acetate; the organic phase was collected, washed with saturated sodium bicarbonate solution, dried with anhydrous sodium sulfate, and concentrated; and the residual oily matter was washed with petroleum ether (25 mL) to obtain a light yellow oily matter 2-((4R,6S)-6-bromomethyl-2-oxo-1,3-dioxane-4-yl)methyl acetate (2.09 g, 75%).

Embodiment 3

(R)-3-hydroxy-5-tert-butyl hexenoate (1.86 g) was dissolved in dichloromethane (20 mL), and added with sodium bromide (2.06 g); $CO_2$ (0.1 MPa) was filled; isopropyl hypochlorite (1.90 g) was added dropwise while stirring the mixture at 25° C.; at the end of dropwise addition of isopropyl hypochlorite, the mixture was stirred for 45 mins while being kept at a certain temperature; at the end of reaction, 10% sodium sulfite solution (15 mL) was added in the mixture; the reaction liquid was extracted with dichloromethane; and the organic phase was collected, washed with saturated sodium bicarbonate solution, dried with anhydrous sodium sulfate, and concentrated to obtain a light yellow solid crude product. The crude product was washed with petroleum ether (25 mL) to obtain a white powdery solid 2-((4R,6S)-6-bromomethyl-2-oxo-1,3-dioxane-4-yl) tert-butyl acetate (2.47 g, 80%).

Embodiment 4

(R)-3-hydroxy-5-tert-butyl) hexenoate (1.86 g) was dissolved in tetrahydrofuran (20 mL), and added with ammonium bromide (1.50 g); $CO_2$ (0.1 MPa) was filled; tert-butyl hypochlorite (3.24 g) was added dropwise while stirring the mixture at −0° C.; at the end of dropwise addition of tert-butyl hypochlorite, the mixture was stirred for 90 mins while being kept at a certain temperature; at the end of reaction, 10% sodium sulfite solution (15 mL) was added in the mixture; the reaction liquid was extracted with ethyl acetate; and the organic phase was collected, washed with saturated sodium bicarbonate solution, dried with anhydrous sodium sulfate, and concentrated to obtain a light yellow solid crude product. The crude product was washed with petroleum ether (25 mL) to obtain a white powdery solid 2-((4R,6S)-6-bromomethyl-2-oxo-1,3-dioxane-4-yl) tert-butyl acetate (2.13 g, 69%).

What is claimed is:

1. A preparation method for 2-((4R,6S)-6-bromomethyl-2-oxo-1,3-dioxane-4-yl)acetate, characterized in that
   a chemical formula of the 2-((4R,6S)-6-bromomethyl-2-oxo-1,3-dioxane-4-yl)acetate (I) is

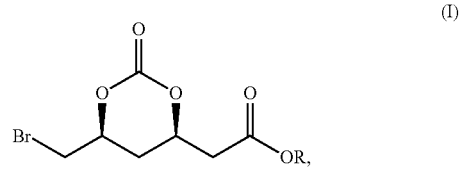

wherein R is alkyl or cycloalkyl having 1 to 8 carbon atoms, or mono- or poly-substituted aryl or aralkyl, wherein 2((4R,6S)-6-bromomethyl-2-oxo-1,3-dioxane-4-yl)acetate (I) is prepared by bromination and cyclization of 3-((substituted oxycarbonyl)oxy)-5-hexenoate as raw material with hypochlorite sad bromide in an organic solvent in presence of $CO_2$, according to following reaction route:

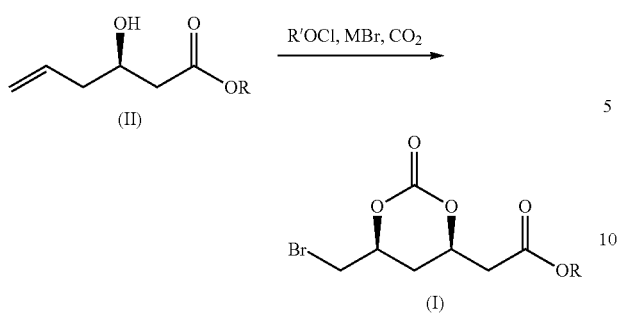

wherein R and R' are same or different alkyl or cycloalkyl having 1 to 8 carbon atoms, or mono- or poly-substituted aryl or aralkyl;

M is alkali metal, alkaline earth metal or ammonium cation; wherein the hypochlorite is selected from one or more of ethyl hypochlorite, isopropyl hypochlorite and tert-butyl hypochlorite;

the bromide is selected from one or more of potassium bromide, sodium bromide and ammonium bromide; and the organic solvent is selected from one or more of ethyl acetate, dichloromethane, tetrahydrofuran, methanol, acetic acid, N,N-dimethyl formamide, acetone and acetonitrile.

2. The preparation method according to claim 1, wherein
a mole ratio of the 3-((substituted oxycarbonyl)oxy)-5-hexenoate (II) to the hypochlorite to the bromide is 1:(1-5):(1-5);
a reaction temperature is −60° C. to 50° C.; and
a reaction time is 10 mins to 180 mins.

3. The preparation method according to claim 1, wherein
the hypochlorite is tert-butyl hypochlorite;
the bromide is potassium bromide; and
the organic solvent is dichloromethane.

4. The preparation method according to claim 2, wherein
the hypochlorite is tert-butyl hypochlorite;
the bromide is potassium bromide; and
the organic solvent is dichloromethane.

5. The preparation method according to claim 2, wherein
a mole ratio of the 3-((substituted oxycarbonyl)oxy)-5-hexenoate (II) to the hypochlorite to the bromide is 1:(1.5-2.5):(1.5-2.5);
a reaction temperature is −40° C. to 25° C.; and
a reaction time is 30 mins to 60 mins.

6. The preparation method according to claim 1, wherein the $CO_2$ is under a pressure of 0.1 MPa to 1 MPa.

* * * * *